(12) United States Patent
Ochi et al.

(10) Patent No.: US 6,569,683 B1
(45) Date of Patent: May 27, 2003

(54) USE OF OXIDATIVE STRESS DIAGNOSTIC PLOT AS A HEALTH INDICATOR FOR ASSESSING OXIDATIVE STRESS AND ITS CONTROL IN HUMANS

(75) Inventors: Hirotomo Ochi, Shizuoka (JP); Richard G. Cutler, Baltimore, MD (US)

(73) Assignee: Nikken Foods Co., Ltd., Shizuoka (JP)

( * ) Notice: Subject to any disclaimer, the term of this patent is extended or adjusted under 35 U.S.C. 154(b) by 0 days.

(21) Appl. No.: 09/463,655

(22) PCT Filed: May 29, 1998

(86) PCT No.: PCT/JP99/02396
§ 371 (c)(1),
(2), (4) Date: Aug. 14, 2000

(87) PCT Pub. No.: WO99/63341
PCT Pub. Date: Dec. 9, 1999

(51) Int. Cl.[7] .............................................. G01N 33/48
(52) U.S. Cl. .............................. 436/63; 436/16; 436/62
(58) Field of Search ............................... 436/16, 62, 63

(56) References Cited

U.S. PATENT DOCUMENTS

| | | | | |
|---|---|---|---|---|
| 5,858,696 A | * | 1/1999 | Roberts, II et al. | 435/25 |
| 5,891,622 A | * | 4/1999 | Morrow et al. | 435/4 |
| 5,912,179 A | * | 6/1999 | Alvarez et al. | 436/63 |
| 5,950,634 A | * | 9/1999 | Ochi et al. | 128/898 |
| 6,096,556 A | * | 8/2000 | Heinecke | 436/89 |
| 6,133,039 A | * | 10/2000 | Heinecke | 436/89 |
| 6,165,797 A | * | 12/2000 | Halstead | 436/128 |
| 6,218,130 B1 | * | 4/2001 | Lamb et al. | 435/7.21 |

* cited by examiner

*Primary Examiner*—Jill Warden
*Assistant Examiner*—Monique T. Cole
(74) *Attorney, Agent, or Firm*—Wenderoth, Lind & Ponack, L.L.P.

(57) ABSTRACT

A diagnostic plot derived from the measurement of 82 assays which characterize two key parameters which significantly contribute to an individual's health status. These two parameters are oxidative stress profile (OSP) and antioxidant profile. Each of the assays which constitute the 82 assays are complimentary with other assays of the profile, thus providing either confirmation information or the synthesis of new information. The diagnostic plot, developed to interpret the assay data which provides information about oxidative damage and antioxidant protection, consists of four quadrants, each with noticeable characteristics. By visually assessing the position of a patient's OSP status, in comparison to reference OSP values in the four quadrants constituting the diagnostic plot, physicians and other health care professionals can provide sound advice to their patients regarding dietary and life style changes one need to adhere for prevention of oxidative stress-related diseases as well as postponing premature aging processes.

1 Claim, 12 Drawing Sheets

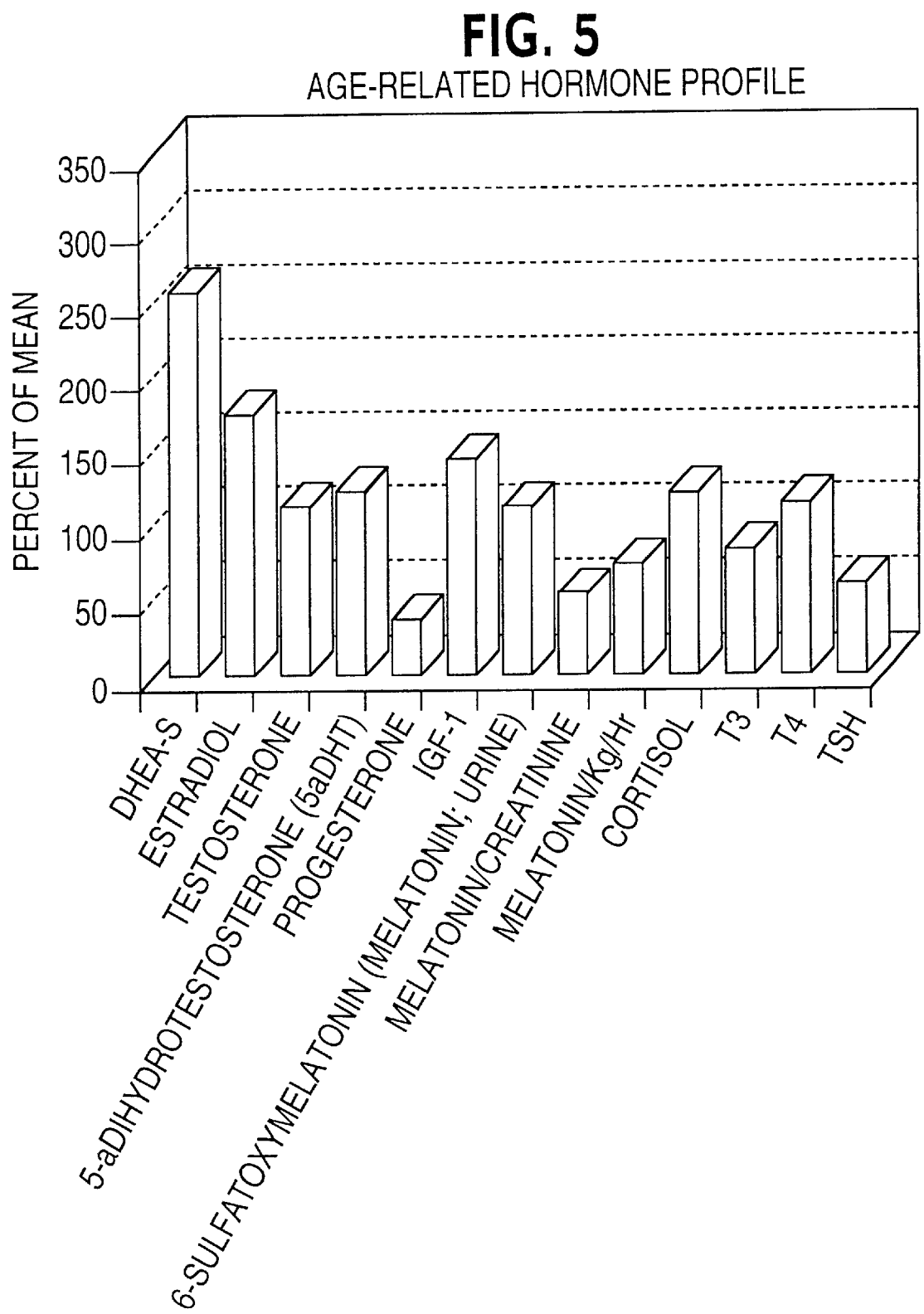

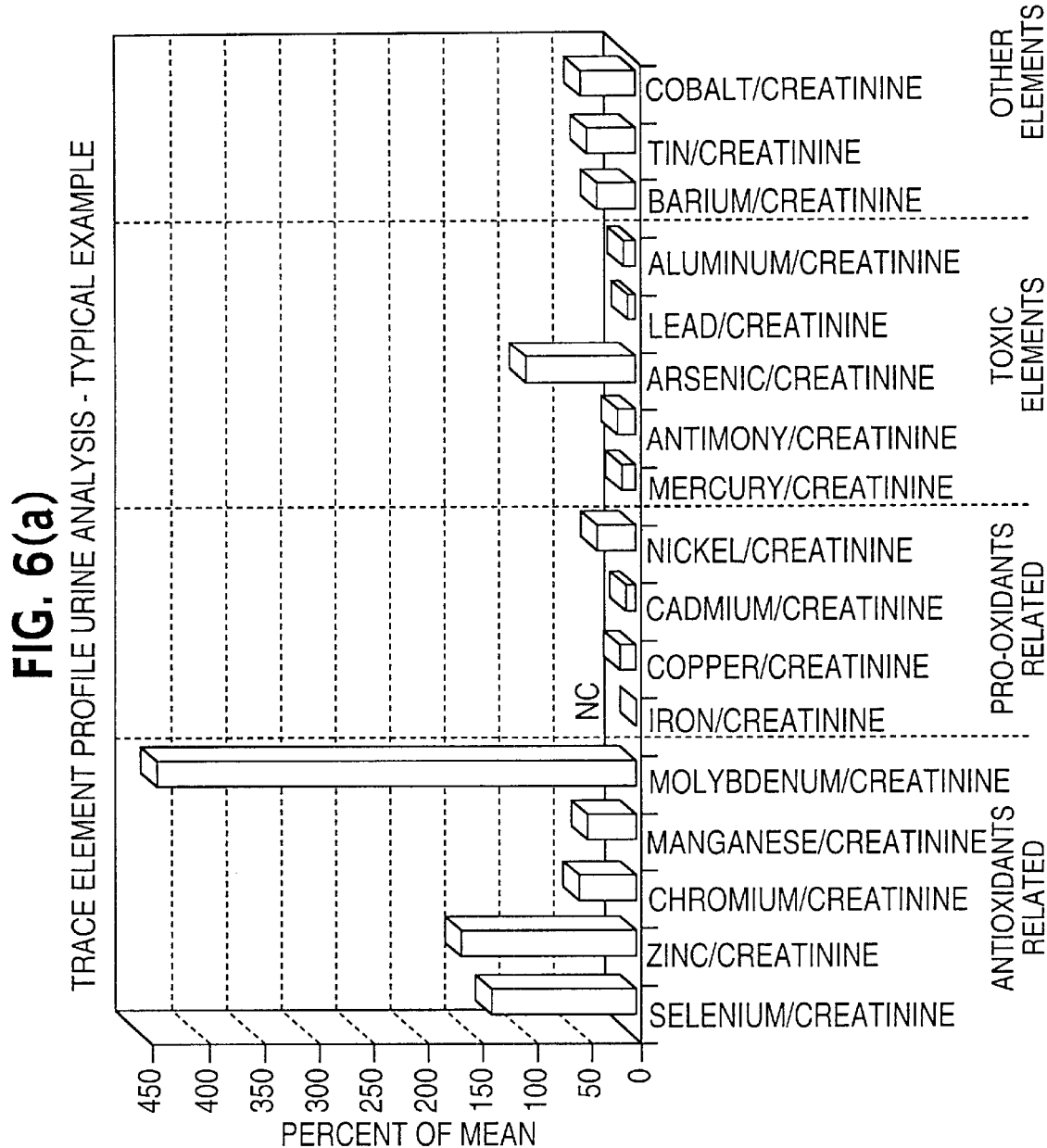

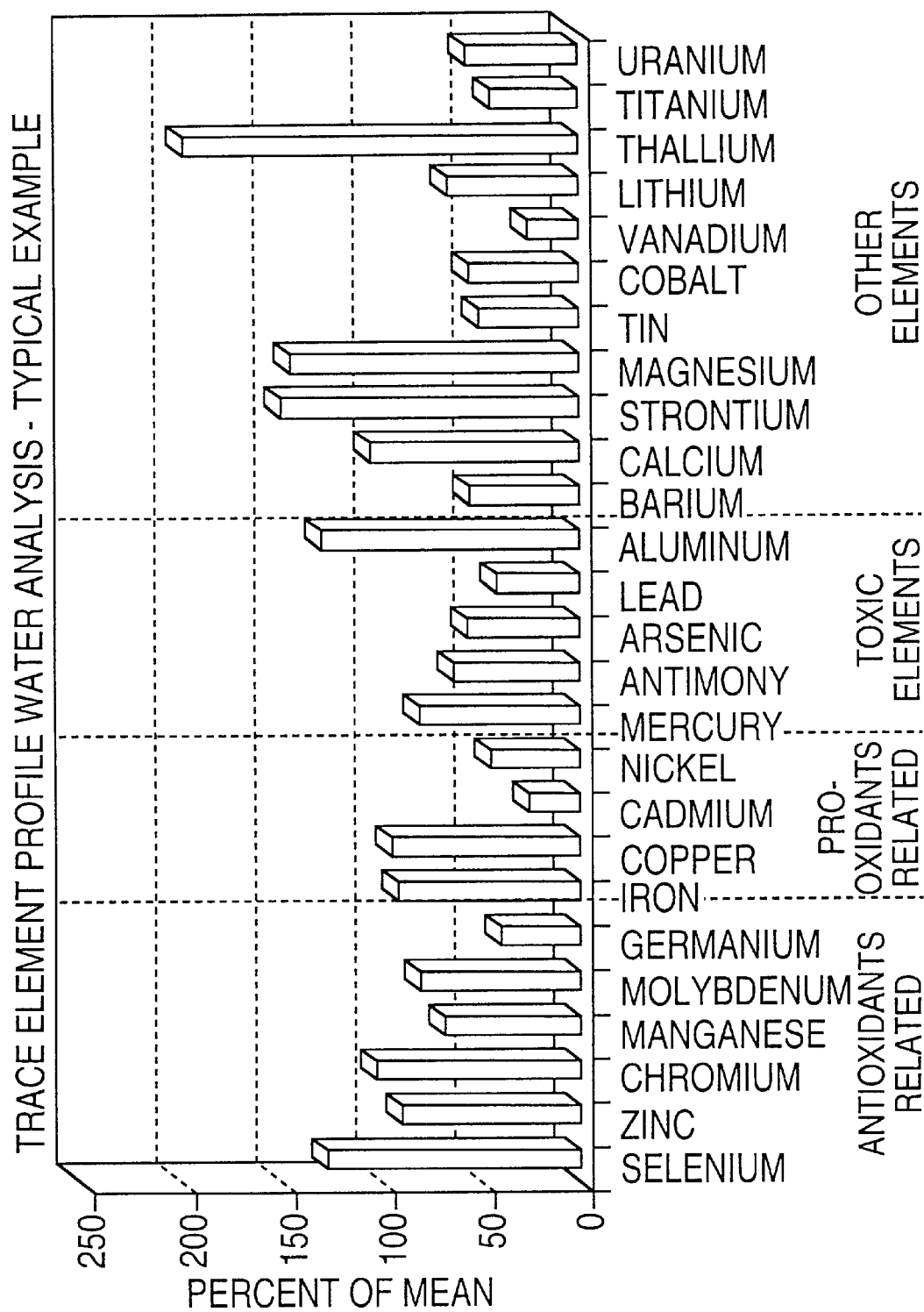

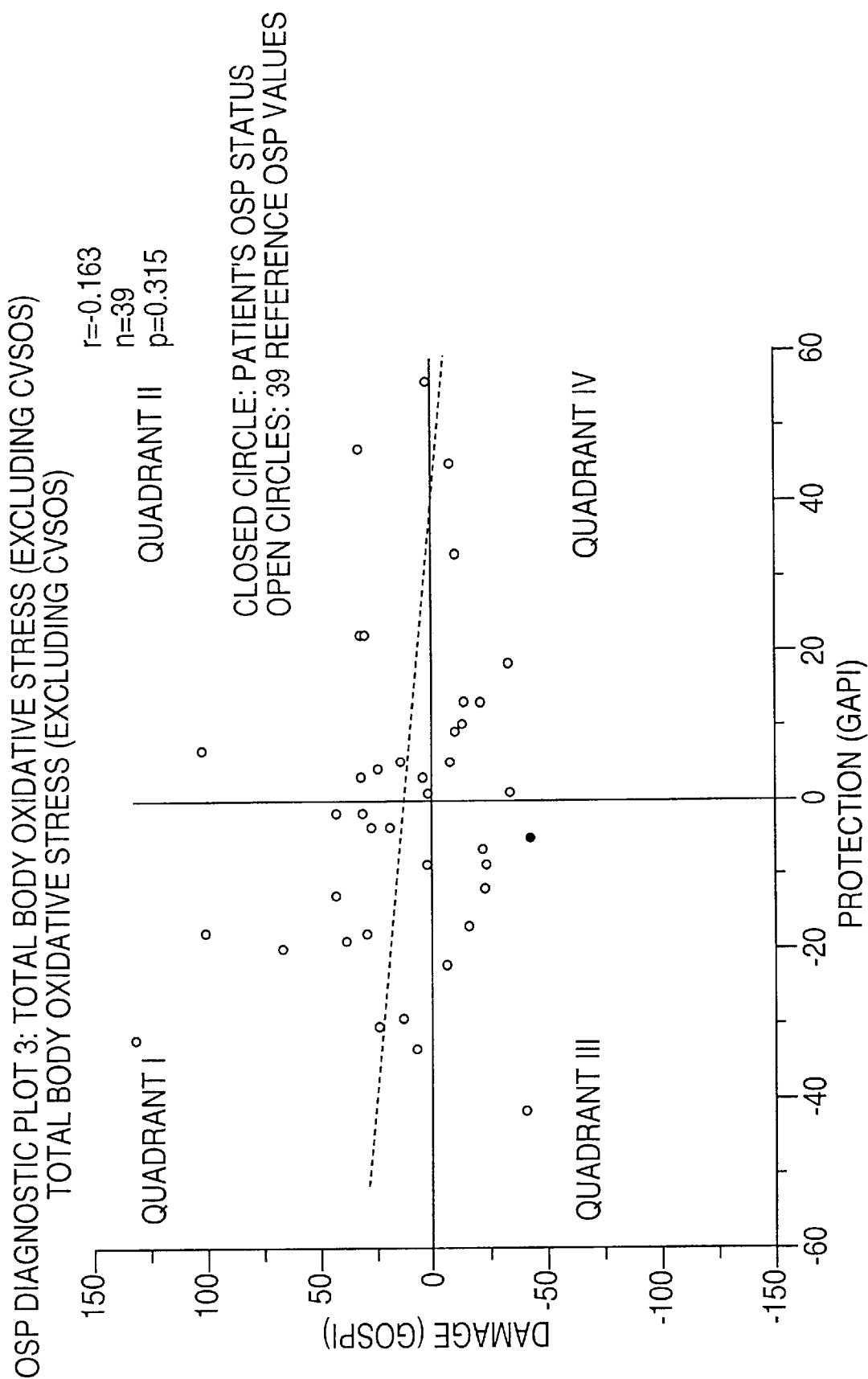

USE OF OXIDATIVE STRESS DIAGNOSTIC PLOT AS A HEALTH INDICATOR FOR ASSESSING OXIDATIVE STRESS AND ITS CONTROL IN HUMANS

TECHNICAL FIELD

All biological constituents of any organism are the result of "trade-offs" of benefits versus disadvantages that have taken place under millions of years of evolutionary pressure. Thus, almost all developmental and metabolic processes that are necessary for the proper function of an organism also have negative side effects that are generally more long term in nature.

The human aging processes themselves now appear to be a result of such trade-offs involving the side reactions of development and energy metabolism. For example, much is known about the harmful side reactions of aerobic metabolism processes in mitochondria, which are very efficient in producing energy. However, free radicals or reactive oxygen species (ROS) are also produced that are toxic by-products of these reactions. If these ROS are not destroyed, they will quickly destroy the cells that produced them.

A compelling body of scientific evidence now indicates that many dysfunctions and diseases in humans are a product of oxidative stress. These include, Aging: Normal aging processes at a higher than normal rate, Segmental progeria disorders (Down's syndrome).

Heart and Cardiovascular Disease: Atherosclerosis, Adriamycin cardiotoxicity, Alcohol cardiomyopathy.

Kidney: Autoimmune nephritic syndromes, Heavy metal nephrotoxicity, Solar radiation, Thermal injury, Porphyria.

Gastrointestinal Tract: Inflammatory and immune injury, Diabetes, Pancreatitis, Halogenated hydrocarbon liver injury.

Eye: Cataractogenesis, Degenerative retinal damage, Macular degeneration.

Lung: Lung cancer (cigarette smoke), Emphysema, Oxidant pollutants (03, N02), Bronchopulmonaly dysphasia, Asbestos carcinogenicity.

Nervous System disorders: Hyperbaric oxygen, Parkinson's disease, Neuronal ceroid lipofuscinoses, Alzheimer's disease, Muscular dystrophy, Multiple sclerosis.

Red Blood Cells: Malaria, Sickle cell anemia, Fanconi's anemia, Hemolytic anemia of prematurity.

Iron Overload: Idiopathic hemochromatosis, Dietary overload, Thalassemia

Ischemia Reflow States: Stroke

Inflammatory-Immune Injury: Glomerulonephritis, Autoimmune disease, Rheumatoid Arthritis.

Liver: Alcohol-induced pathology, Alcohol-induced iron overload injury.

Other Oxidative Stress Disorders: AIDS, Radiation-induced injuries (accidental and radiotherapy), General low-grade inflammatory disorders, Organ transplantation, Inflamed rheumatoid joints, Arrhythmias, Myocardial infarction The general age-dependent decline in optimum health and performance (known as normal aging) appears to be the result of ROS, which is one of its major causative factors. In addition, many different types of bacterial, fungal and viral infections increase the amount of ROS generated in vivo. Sometimes this increase is dramatic (as in AIDS), but it also can be very slight as in a number of low-grade bacterial and fungal infectious diseases.

BACKGROUND ART

Basic Concept of Oxidative Stress Profile (OSP) Oxidative stress (OS) is defined as the steady-state level of oxidative damage within a cell, tissue or organism caused by ROS. The degree of oxidative stress or the oxidative stress state (OSS) present in a given biological system is determined by the net result of three major factors. These three factors, identified in FIG. 1, are:

(1) Initial rate of generation of ROS (2) Level of antioxidant protective processes (3) Rate of repair and general turnover or removal rate of the oxidized targets that Include nucleic acids, proteins and lipids.

Many of the oxidized damage components that are produced throughout the body are transported to the serum, urine or breath, as denoted by (4) in FIG. 1. The OSS, as denoted by (5) in FIG. 1, can refer to any component or system such as the whole individual, an organ, a tissue, a cell or a subcellular fraction. It is the ratio of damage input, [denoted by (6)], to damage output [denoted by (7)] that determines the OSS value. This ratio is largely controlled by a specific set of genes known as "longevity determinant genes". Diet also offers an effective means of control if it is known what dietary factors are most important and what is best for each individual.

The concept of OSS is fundamental to understanding the health maintenance in humans because it determines the probability that initiation of abnormal functions and diseases will occur over time, as denoted by (8) in FIG. 1. Since initiation and rate of progression with age of major diseases is strongly related to an individual's characteristic OSS, control of OSS is key to the control of human health and longevity. To achieve this aim, there is a growing need within the scientific and clinical medical communities for (a) specific, reliable, non-invasive and cost-effective assays that are effective in measuring small changes of OSS, and (b) a unique, integrated set of these assays that can be used to calculate most effectively an individual's OSS.

DISCLOSURE OF INVENTION

The invention reported here is given the name, Oxidative Stress Profile (OSP). The OSP provides the most complete set of assays designed to assess the OSS of an individual. These assays are designed for use by (a) the scientific community in basic research, (b) practicing clinicians and medical doctors, and (c) individuals interested in personally optimizing their health and longevity. The OSP is made up of 10 components, each consisting of assays for 2–22 biomarkers of health. These 10 components and the number of biomarkers specific for each component are identified as follows:

1. spot screening (biomarkers #1–7)
2. prooxidant potential (biomarkers #8–14)
3. glycation potential (biomarkers #15–16)
4. total antioxidants (biomarkers #17–20)
5. water-soluble antioxidants (biomarkers #21–24)
6. lipid-soluble antioxidants (biomarkers #25–38)
7. lipids and proteins (biomarkers #3943)
8. cardiac disease risk factors panel (biomarkers #44–50)
9. age-related hormone panel (biomarkers #51–60)
10. mineral and trace element panel (biomarkers #61–82).

Each of the assays used are complimentary with other assays of the profile, thus providing either confirmation information or the synthesis of new information. Thus the diagnostic value of the sum of the assays used in the OSP is much greater than the individual parts. A new technique called the Genox Oxidative Stress Profile Diagnostic Plot (GOSP Diagnostic Plot) has been developed to interpret the assay data from OSP. The GOSP Diagnostic Plot is based on the calculations of two key parameters from an individual OSP.

The first parameter is called the Genox Oxidative Stress Profile Index (GOSPI). It is calculated from 8–10 of the oxidative damage and prooxidant potential assays and represents the average level of oxidative damage with reference to the 100 percent mean level. That is:

$GOSPI=1/n\Sigma$(Percent of Mean—100%), where n is equal to number of assays in the sum.

The second parameter is called the Genox Antioxidant Profile Index (GAPI). It is calculated from 20–30 of the antioxidant assays and represents the average level of antioxidant protection with reference to the 100 percent mean level. That is:

$GAPI=1/n\Sigma$(Percent of Mean—100%), where n is equal to number of assays in the sum.

The GOSPI and the GAPI are then plotted on an XY axes to illustrate their relation with reference to about an 300 individuals having similar GOSP Diagnostic Plots. This is shown in FIG. 2.

The diagnostic plot consists of four quadrants, each with noticeable characteristics.

Quadrant I: Individuals in this quadrant have the expected high level of oxidative stress that accompanies low levels of antioxidants. They are therefore expected to respond to higher dosages of antioxidants, as illustrated to lower their OSS.

Quadrant II: Individuals in this quadrant have high OSS levels in spite of above average levels of antioxidant protection. The data obtained from experimental study suggest that this condition is quite common and represents one of the most important applications of the OSP. This condition could develop as a result of stress occurring due to,
(a) High levels of iron and/or copper stress
(b) High levels of inflammatory related disease such as caused by microorganism infections (bacterial, viral low grade infection; examples are AIDS and malaria)
(c) Pharmacological drugs that block antioxidant absorption or synthesis or generate ROS.
(d) Alcoholism
(e) Exposure to toxic environmental factors as trace metals, asbestos.
(f) Oxidative stress related diseases, such as diabetes.

Quadrant III: Individuals in this quadrant have lower than normal OSS, but with a low antioxidant state. This represents an optimal health state, and suggests that even future improvement can be realized through increasing the antioxidant levels. Such cases also indicate that all the relevant antioxidants (most of which are in tissues other than blood) may not be being measured.

Quadrant IV: Individuals in this quadrant have lower than normal OSS, with the expected accompaniment of higher than normal levels of antioxidant protection. Further improvement may be indicated by increasing antioxidants in diet, or possibly lowering endogenous production of antioxidants. What action is best will be indicated by the detail of an individual's OSP.

In summary, by utilizing the Genox OSP diagnostic plot, along with the specific details of the OSP, the physicians will possess a powerful tool to assist them in the proper treatment of their patients. Since each human is unique as to their heredity, lifestyle and environment exposure, their needs are also unique. The Genox OSP diagnostic plot is a unique tool designed to evaluate the oxidative stress in humans.

BRIEF DESCRIPTION OF DRAWINGS

FIG. 5 is an Age-related Hormone Profile;

FIG. 6(a) is a Trace Element Profile with respect to Urine.

FIG. 7(b) is a Trace Element Profile with respect to Water;

FIG. 10 is an Oxidative Stress Profile (OSP) Diagnostic Plot 3: Total Body Oxidative Stress (excluding CVSOS).

BEST MODE FOR CARRYING CUT THE INVENTION

Figure 1:
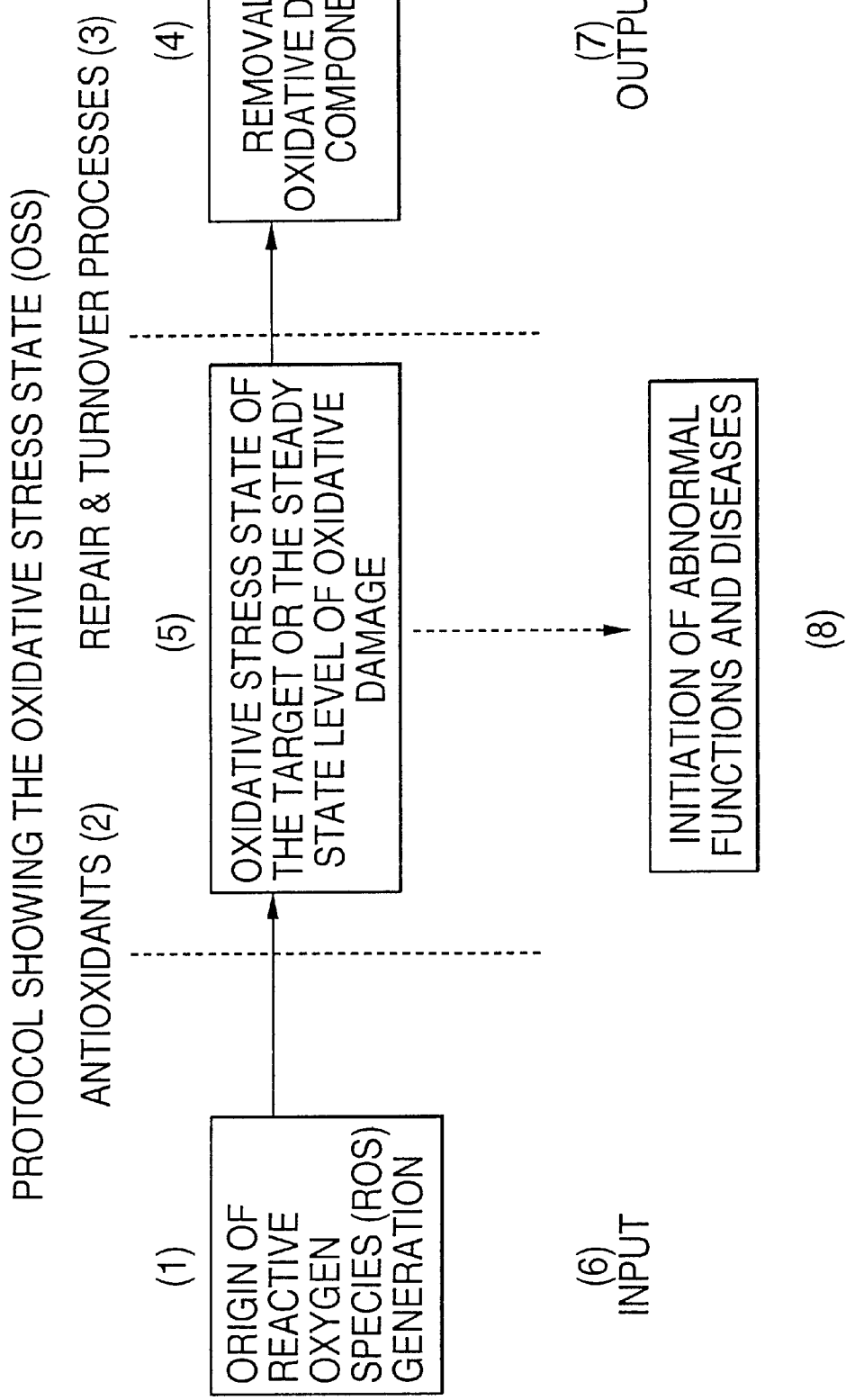
FIG. 1 is a protocol showing the Oxidative Stress State (OSS)

Accurate Determination of Oxidative Damage Oxidative damage is a major contributing factor in the onset of age-related degenerative diseases. Assays that measure many different types of oxidative damage that can be used as a diagnostic tool of optimizing a person's health and longevity are essential in assessing an individual's oxidative stress status. By measuring many different biomarkers collectively, the most accurate and comprehensive indication of the general level of oxidative stress in a patient can be profiled. Analysis of each individual type of damage can give a more specific indication of the exact risk and prevention strategies that can be prescribed.

Ten components of the OSP and the biomarkers which constitute each of these components are briefly described below.

Spot Screening

1. Total Alkenals (in serum and urine)—measures products of lipid peroxides (malonaldehyde ad 4-hydroxynonenal) from free radical attacks on cellular lipid membranes and lipoproteins (i.e. LDL). The measure of the amount of serum lipid peroxides reflects the amount of free radical damage in the body.

2. Aqueous Hydroperoxides (in serum)—directly measures aqueous such as hydrogen peroxide, which can react with prooxidant metals to form the very reactive hydroxyl radical. The measure of the amount of serum hydroperoxides reflects the amount of free radicals being produced in the body at that time.

3. Lipid Hydroperoxides (in serum and urine)—directly measures lipid hydroperoxides [not hydrogen peroxide or products of lipid peroxide damage, i.e. aldehydes (MDA)]. The measure of the amount of serum lipid hydroperoxides reflects the amount of free radicals being produced in the body at that time.

4. Auto-antibody oxidized-LDL (in serum)—The current and predominant theory of the development of cardio-vascular disease is that LDL becomes oxidized, gets engulfed by a monocyte which becomes a 'foam' cell that then gets stuck in the arterial cell wall and causes a fatty acid streak lesion (plaque). Oxidized LDL (Ox-LDL) induces an immune response to remove it from the body. The immune response is directly proportional to the amount of Ox-LDL present throughout the body. Because most of the Ox-LDL is in the arterial cell wall, it is not very effective to measure it in the serum; therefore, the auto-immunity antibody assay toward Ox-LDL is now recognized as a very powerful risk predictor of cardiovascular disease.

5. 8-hydroxy deoxyguanosine [8-OH dG] (in urine)—is the 'gold' standard for measuring oxidative damage, within the cell, to chromosomal and mitochondrial DNA. 8-OH dG is a hydroxyl radical-damaged guanine nucleotide that has been excised from DNA by endo-nuclease repair enzymes, and reflects a person's DNA mutation potential and therefore, cancer risk. Since repair is known to normally occur quickly and efficiently, the amount of excised DNA adducts in serum or urine directly reflects the amount of damage within the entire body.

6. 8-epi-prostaglandin $F_2$ [isoprostane] (in urine)—is formed in vivo by the free radical catalyzed non-enzymatic peroxidation of arachidonic acid in cellular membranes and lipoproteins (i.e. LDL). The damaged lipid peroxide is excised from the cell wall into the serum and then excreted in urine. Unlike the reactive aldehydes, once isoprostanes are formed, they are chemically stable and can be accurately measured in serum or urine. 8-epi '$PGF_2$ formation is unaffected by aspirin consumption and has been shown to be a sensitive measure of oxidative stress and the effectiveness of antioxidant supplementation.

7. Creatinine (in urine)—is used to calculate the patient's metabolic efficiency [amount of free radical production (damage) per energy utilized (ATP synthesis)] .Creatinine is a product of the breakdown of ATP/creatinine utilization which is excreted in the urine. 12 to 24 hr. urine creatinine values are used to calculate the amount of damage being produced relative to the amount of energy or activity of that person (ratio). 12–24 hr urine creatinine values reflect a person s basal metabolic rate. Dividing creatinine by a person's lean body mass gives the amount of metabolic activity (ATP utilization) per cell over a given period of time.

Prooxidant Potential

8. Total Iron—Unbound rion can act as a prooxidant by catalyzing the production of the very reactive hydroxyl radical from hydrogen peroxide and strong reducing agents such as ascorbate or homocysteine (Fenton reaction). High iron (overload) is associated with high amounts of free radical damage and a high risk for developing most of the age-related diseases such as diabetes, heart disease and cancer.

9. Available Iron Binding Capacity (AIBC)—is the amount of transferrin, ferritin and albumin that is not binding iron and therefore can accept (capture) a free iron molecule. Iron binding proteins are known to be a very effective prevention of iron -catalyzed free radical production. High AIBC offers good protection against the initiation of oxidative damage reactions. AIBC proteins are synthesized in the liver and are kept at a fairly constant steady state level in the serum; generally the higher the iron (iron bound by proteins), the lower the AIBC.

10. Total Iron Binding Capacity (TIBC)—is represented by the value; AIBC+Total Iron. This value is used to reflect the liver's capacity in making iron-binding proteins.

11. Percent Iron Saturation—(total iron/TIBC) in percent. This is the relative ratio of iron to iron binding capacity; the higher the iron saturation, the higher the risk for iron to participate in catalyzing free radical species.

12. Ferritin—is an iron binding protein synthesized by the liver in response to the amount of iron in the serum. Ferritin is an indicator of the body's iron storage and possible long-term iron overload. High ferritin levels in serum have been associated with high amounts of free radical damage and a higher risk for developing most of the age-related diseases such as diabetes, heart disease and cancer.

13. Copper—Unbound copper is known to be an even more reactive prooxidant than iron, especially in the presence of strong reducing agents such as ascorbate (vitamin C) or homocysteine. High copper levels in serum can induce and is associated with high levels of oxidative damage. Small amounts are required for CuZn-superoxide dismutase and ceruloplasmin.

14. Cerlloplasmin—Binds up to 95% of the copper found in serum. In normal patients, the amount of ceruloplasmin is directly proportional to the amount of copper in the serum, high copper concentration being usually associated with high amounts of lipid peroxidation and risk for cardiovascular disease. Ceruloplasmin is thought to be an antioxidant in that, it acts as a ferroxidase (oxidizes free iron) thereby inhibiting it from participating as a prooxidant and is essential in removing excess iron from the body. Ceruloplasmin also acts as a superoxide dismutase. A decrease of ceruloplasmin is seen in Wilson's disease.

Glycation Potential

15. Glucose—Glucose levels indicate that the patient is fasting or may indicate uncontrolled diabetes mellitus or hypoglycemia.

16. Glycated Protein (Fructosamine)—is used to measure the average blood glucose levels over the last 1–3 weeks prior to sample collection time. This assay measures all of the glycated proteins in serum [total proteins including albumin, but not hemoglobin (RBC) which are only in whole blood]. The amount of glycated proteins increases with oxidative stress and aging.

Total Antioxidants

17. Oxygen Radical Absorption Capacity [ORAC] (in serum and saliva)—measures the total antioxidant capacity in a sample. The 95% ORAC value represents the fast acting antioxidants in the serum, which constitutes the first line of defense. These include ascorbate, thiols, uric acid, bioflavonoids, polyphenols etc. The 50% ORAC value represents the fast and medium acting antioxidants used by the serum, which includes the moderately active antioxidants such as albumin and lipids.

18. Aqueous ORAC—measures the antioxidants in a serum sample after the removal of proteins and lipids. Because of their abundance, almost half of the whole serum ORAC value is from proteins and lipids. Most proteins and lipids are not very active antioxidants (sacrificial) and decrease the sensitivity of the ORAC assay in measuring less abundant but more active antioxidants. Removing the lipids and proteins from the serum sample increases the sensitivity of the ORAC assay in measuring the other aqueous soluble antioxidants.

19. Lipid ORAC—measures the antioxidants in a serum sample after the removal of proteins and the aqueous phase of the sample. Because of their abundance, over half of the whole serum ORAC value is from proteins and aqueous antioxidants. Removing the proteins and aqueous antioxidants from the serum sample increases the sensitivity of the assay on measuring the lipid soluble antioxidants.

20. Lipid Peroxidation Inhibition Capacity [LPIC] assay—Plasma antioxidants can be classified into two major types: (a) primary antioxidants such as ceruloplasmin and transferrin, which reduce the initiation rate of lipid peroxidation by binding prooxidant metals, and (b) secondary antioxidants such as tocopherol, which reduces the chain propagation and amplification of lipid peroxidation. Many antioxidants also have multiple antioxidant properties such as uric acid, which can bind many prooxidant metals as well as directly scavenging oxidized species. The LPIC assay measures the activity of both the primary and secondary antioxidant systems as they are working together in a sample. In humans, low serum LPIC values has been shown to strongly predict the development of adult-onset diabetes.

Water-soluble Antioxidants

21. Vitamin C [Ascorbate] (in serum and saliva)—Ascorbic acid can directly scavenge oxidative species as well as generate other oxidized antioxidants such as vitamin E. However, under conditions where there are free prooxidant metals around, such as iron and copper, vitamin C's strong reductive capacity will catalyze the production of oxidtive free radicals.

22. Thiols (in serum and saliva)—are very active antioxidants and reducing agents. Most serum thiols are found in albumin followed by free cysteine and glutathione. Albumin thiols are thought to act as sacrificial antioxidants that have little biological consequences of being damaged. Because of their high antioxidant reactivity and high concentration, albumin thiols act as a major defense against free radical damage to cell membranes.

23. Uric acid (in serum and saliva)—Uric acid is a methylxanthine (like caffeine) which stimulates brain activity. It is also known to directly scavenge oxidative species and chelate prooxidant metals.

24. Direct and Total Bilirubin:—considered as a waste product of heme metabolism. Bilirubin is known to be a very active lipid and aqueous soluble serum antioxidant. Direct (conjugated) bilirubin is the form of bilirubin that can be absorbed and removed from the body in the bile.

Lipid-soluble Antioxidants

25. Lutein:—A very active lipid-soluble carotenoid antioxidant (2.3 times higher than vitamin E), which is readily absorbed into the serum. Lutein and zeaxanthin are major factors in the prevention of macular degeneration, which is the leading cause of blindness in the elderly and represents 10% of all blindness in humans.

26. Zeaxanthin:—A very active lipid-soluble carotenoid antioxidant (2.8 times higher than vitamin E) which is readily absorbed into the serum. Lutein and zeaxanthin are implicated in the prevention of macular degeneration, which is the leading cause of blindness in the elderly and represents 10% of all blindness in humans.

27. β-Cryptoxanthin:—Probably the most active of the lipid soluble antioxidants (3.1 times higher than vitamin E) which is readily absorbed into the serum.

28. Lycopene:—One of the most active lipid-soluble antioxidants (2.8 times higher than vitamin E). Research has indicated that lycopene may be very important in the prevention of prostate cancer.

29. α-Carotene:—A known antioxidant and precursor to vitamin A. Experimental evidence shows that □-carotene is a stronger antioxidant and cellular differentiating agent than b-carotene and therefore may be better in preventing cancer.

30. βCarotene:—A known antioxidant and precursor to vitamin A, which has been most widely researched and used extensively as a diet supplement. It is a strong cellular differentiating agent, and therefore may prevent cancer.

31. Retinol [Vitamin A]:—A known antioxidant and cellular differentiating agent and Therefore may prevent cancer and many aspects of aging.

32. Retinyl Palmitate:—The retinol ester that is most commonly used in dietary Supplements and foods as a source of vitamin A.

33. Carotenoid classes:—This grouping of carotenoids contain many uncharacterized carotenoids that most likely are beneficial to health. This value provides a good overall value of the amounts of fruits and vegetables being consumed.

34. α-Tocopherol (Vitamin E):—One of the best characterized and diet supplemented lipid-soluble antioxidants. Apart from its antioxidant capabilities, it has cellular differentiation properties which are believed to be good in preventing cancer.

35. δ-Tocopherol (Vitamin E):—Not much is known about the beneficial effects of δ-tocopherol to humans, though it is normally found at lower amounts in foods and human serum.

36. γ-Tocopherol (Vitamin E):—The major type of vitamin E found in the heart and therefore may be selected for the body because of its unique properties either as an antioxidant or as a differentiation agent.

37. Tocopherol/(Cholesterol+Triglycerides):—The ratio of lipid antioxidants per Amount of lipids that there is to be protected. This type of parameter has been found to give a much better indication of risk for developing cardiovascular disease than by evaluating these biomarkers alone.

38. Ubiquinol [Coenzyme Q10]:—is normally synthesized in cells as part of the mitochondrial oxidative phosphorylation system and is present in lipid biomembranes. COQ10 can also be absorbed through the diet and can act as a very active antioxidant and protecting LDL from becoming oxidized.

Lipids and Proteins

39. Cholesterol:—Cholesterol is a well-known risk predictor for cardiovascular disease by indicating the amount of lipids that can potentially be oxidized. The current theory of the development of cardiovascular disease is that LDL becomes oxidized, gets engulfed by a monocyte which becomes a 'foam' cell that gets stuck in the arterial cell wall and causes a fatty acid streak lesion (plaque).
40. Triglycerides:—Triglcerides are esters of fatty acids and glycerol bound to proteins called lipoproteins. Triglycerides and cholesterol both measure the total amount of lipoproteins in the serum, which can be a rough indicator of risk for cardiovascular disease. The associated cardiovascular disease risk prediction offered by triglycerides and cholesterol by themselves is actually low (44%); but, in conjunction with vitamin A and E, the ratio of (cholesterol+triglycerides)/(vitarnin A and E) elevates the risk predictive power to 85% accuracy.
41. Albumin:—Each albumin molecule contains many very active thiol groups that act as potent antioxidants. Albumin is known as a sacrificial antioxidant because it has no recycling pathway and the consequences of its damage do not directly affect cellular function. Albumin has a high turnover rate; damaged albumin is degraded and the body reuses the good amino acids. Most other antioxidant mechanisms use some sort of direct regeneration system (i.e. vitamin E, vitamin C and glutathione peroxidase).
42. Total Protein:—Includes albumin and the immunoglobulins. Thus, the amount of globulins in a serum sample can be calculated from the simple equation, Amount of globulin=Total Protein−Amount of albumin
43. Albumin/Globuihn ratio:—is used as a general marker of health and well being. The ideal ratio is 1.85 or higher. High immunoglobulins can indicate a long history of infections, which may increase the risk of developing autoimmune diseases.

Cardiac Disease Risk Factors Panel

44. Homocysteine:—Homocysteine is a strong reducing agent and can promote pro-Oxidant metal catalyzed production of free radicals. Elevated levels of homocysteine are highly associated with a high risk of cardiovascular disease. In most patients high homocysteine is caused by deficiencies in folic acid and/or vitamin $B_{12}$.
45. Folic Acid:—Folic acid is involved in DNA synthesis, red blood cell Regeneration and homocysteine metabolism. Low levels are associated with birth defects, DNA damage and accumulation of homocysteine. Deficiency results in high-elevated DNA mutation rate, oxidized LDL, irreversible nerve degeneration and anemia. Folic acid and vitamin $B_{12}$ are synergistic in their actions.
46. Vitamin $B_{12}$ [cyanocobalamin]:—Vitamin $B_{12}$ is involved in DNA synthesis, red Blood cell regeneration and homocysteine metabolism. Low levels are associated with birth defects, DNA damage, and accumulation of homocysteine. Deficiency results in high-elevated DNA mutation rate, oxidized LDL, irreversible nerve degeneration and anemia Vitamin $B_{12}$ and folic acid are synergistic in their actions.
47. Low Density Lipoproteins (LDL):—Known in popular literature as the 'bad' Cholesterol, LDL is directly associated with risk for heart disease. Prevention of LDL from becoming oxidized can be achieved by decreasing free prooxidizing metals, increasing water-soluble antioxidants (albumin, uric acid and vitamin C) and lipid-soluble antioxidants (vitamin A, vitamin E, CoQ10and carotenoids).
48. High Density Lipoproteins (HDL):—Known in popular literature as the 'good' Cholesterol, HDL is inversely associated with risk for heart disease.
49. Apolipoprotein B:—is a protein found primarily on LDL and therefore is actually a measure of LDL.
50. Apolipoprotein A1:—is a protein found primarily on HDL and therefore is actually a measure of HDL.

Age-related Hormone Panel 51. 5-Dihydrotestosterone:—is a toxic form of testosterone known to cause male pattern baldness and to damage prostate cells, which increases the risk of prostate cancer.
52. 6-hydroxymelatonin sulfate [6-SM] (in urine):—Cycling melatonin levels have been shown to decrease with age and therefore has recently become a very popular supplement for antiaging strategy and to induce natural sleep. Melatonin also has been demonstrated to possess antioxidant properties that may be directed to neurons. Serum melatonin levels have many cyclic peaks throughout the day and night; a single determination of serum/saliva melatonin is not very accurate in determining inadequate or excessive release of melatonin. Melatonin is metabolized to 6-hydroxyrnelatonin sulfate, a highly stable end product which is excreted in urine. A timed 12 or 24 urine collection is the most accurate step to measure a person's melatonin excretion levels.
53. Cortisol:—Cortisol is a steroid hormone that is elevated during many different types of stress including oxidative stress. Long term exposure to elevated levels of cortisol has been shown to accelerate the signs of aging.
54. Dehydroepiandrosterone sulfate [DHEAS]:—DHEA is known as the master Hormone since it is a precursor for the synthesis of many other hormones. As DHEA-S level has been demonstrated to decrease with age, it has recently become a very popular dietary supplement used to raise the hormone levels to the range seen in youthfuil phase of life. DHEA-sulfate is the form that is normally stored in the body and therefore this supplement has less negative side effects compared to supplementing DHEA directly.
55. Estradiol:—Estradiol is linked with a high risk of developing breast cancer, Especially in post-menopausal women, who take excess of supplements. Other forms of estrogen are reported to be safer. Women with chronically higher amounts of circulating estradiol have been known to reach menopause much earlier than normal.
56. Insulin-like Growth Factor—1 [IGF-1] or Somatomedin C:—IGF-1 mediates the effects of human growth hormone (HGH), such as stimulating cellular renewal, repair and growth. In normal patients, IGF-1 is produced in the liver in amounts directly proportional to growth hormone. Due to its long half-life, IGF-1 can be used to measure the average amount of growth hormone released within the last 48 hours. Because HGH has many cyclic peaks throughout the day and night, a single serum determination of HGH is not very accurate in determining inadequate or excessive release of HGH. HGH and IGF-1 injections have been shown to help the elderly rebuild muscle and strength, thereby improving their quality of life.

57. Progesterone:—Progesterone is currently a popular supplement believed to enhance memory and cognitive functions.
58. Testosterone:—Testosterone is responsible for the expression and maintenance of most adult male characteristics, such as facial hair and muscle growth. However, testosterone can be converted in some cells, like hair follicles and prostate cells, to a toxic form (dihydrotestosterone, DHT) which is damaging to these cell types.
59. Thyroid Stimulating Hormone (TSH) third generation:—TSH stimulates the uptake of iodine by thyroid cells.
60. Thyroxine (T4):—Thyroxine is a global steroid hormone that regulates metabolic Rate and indicates proper thyroid function. The synthesis of thyroxine from iodine produces hydrogen peroxide as a by-product. Those suffering from hyperthyroidism hae been shown to have signs of accelerated aging.

Mineral and Trace Element Panel

61. Aluminium:—Accumulation of aluminium in the brain has been strongly associated with the onset of Alzheimer's disease. This is thought to be an effect of the disease rather than a cause.
62. Antimony:—Antimony is a toxin, and has no known human need.
63. Arsenic:—Arsenic is a well known poison that inhibits respiration.
64. Cadmium:—Cadmium is a well known toxin, similar to mercury, and has no known human need.
65. Calcium:—Calcium aids in apoptosis, blood clotting and nerve signaling. Low serum amounts are known to cause osteoporosis, poor growth and maintenance of bones and teeth.
66. Chromium:—Industrial chromium [$Cr_{+6}$] is a very toxic prooxidant. Small amounts of $Cr^{+3}$ are required in glucose tolerance proteins and finctions to regulate blood glucose levels.
67. Cobalt:—Cobalt is a component of vitamin B12. It can be toxic at high levels.
68. Copper:—Unbound copper is known to be even more reactive prooxidant than iron, Especially in the presence of strong reducing agents such as ascorbate or homocysteine. High levels of copper can induce oxidative damage. Small amounts are required for CuZn-superoxide dismutase and ceruloplasmin.
69. Iodine:—Iodine is required for synthesis of the thyroid hormone thyroxine, which Produces hydrogen peroxide as a byproduct. Iodine is a halogen (like fluorine and chlorine) and can readily act as a free radical generator. High amounts of iodine can be very toxic.
70. Iron:—Unbound iron can act as a prooxidant by catalyzing the production of the very reactive hydroxyl radical from hydrogen peroxide and strong reducing agents such as ascorbate and homocysteine. High iron (overload) is associated with high amounts of free radical damage and a higher risk for developing most of the age-related diseases such as diabetes, heart disease and cancer.
71. Lead:—Lead is a well known neurotoxin that has no known human need.
72. Magnesium:—Magnesium is necessary for RNA/DNA synthesis, protein synthesis, ADP synthesis and muscle contraction. Since it has a fixed outer electron valence of +2, it can inhibit many iron based free radical generating reactions by displacing iron from its binding site. Magnesium has been shown to be helpful in preventing heart disease.
73. Manganese:—Unbound manganese is known to be a strong prooxidant, especially in the presence of strong reducing agents such as ascorbate or homocysteine. It is toxic at high levels. Small amounts ae required for Mn-superoxide dismutase.
74. Mercury:—Mercury is a well known neurotoxin that has no known human need.
75. Molybdenum:—Molybdenum is required by xanthine oxidase in converting xanthines to uric acid. It is also required in aldehyde oxidase and sulfite oxidase in oxidizing these toxic compounds into less reactive products. Oxidases produce hydrogen peroxide as a byproduct of their reaction.
76. Nickel:—Unbound nickel is known to be a strong prooxidant and is toxic at high levels. Small amounts are required for red blood cells and liver function.
77. Selenium:—Unbound selenium is known to be a prooxidant with similar valences as oxygen. It is toxic at high levels. Small amounts are required for glutathione peroxidase.
78. Sulfur:—Sulfur is essential for protein structures and enzyme activity; it is also Required in many detoxification reactions and can lower a person's risk of developing cancer.
79. Strontium:—Strontium is known to inhibit vitamin D synthesis; therefore it can be an important risk factor for osteoporosis and bone malformation in developing children.
80. Tin:—Tin is required for proper metabolism and growth of bone and teeth.
81. Vanadium:—Vanadium is involved in lipid metabolism. Deficiency of vanadium has been shown to increase cholesterol levels (high doses did not lower cholesterol past their normal set point). Current studies are evaluating vanadium ability in killing cancer cells. Vanadium can be toxic at high levels.
82. Zinc:—Zinc is necessary for metabolism, RNA polymerases and CuZn-superoxide Dismutase. Because it has a fixed outer electron valence of +2, it can inhibit many iron based free radical reactions by displacing iron from its binding site. Zinc can be toxic at high levels.

Almost all of the 82 biomarkers (which are directly determined from the test samples) are measured by the most accurate, recently established biochemical assays using sophisticated, automated instruments.

Specific details about these assays are listed below.

| Biomarker | Assay used for determination |
|---|---|
| Spot Screening | |
| 1. Total alkenals | spectrophotometric/chemical |
| 2. Aqueous hydroperoxides | spectrophotometric/chemical |
| 3. Lipid hydroperoxides | spectrophotometric/chemical |
| 4. Auto-antibody oxidized-LDL | spectrophotometric/immunochemical |
| 5. 8-hydroxy deoxyguanosine | spectrophotometric/immunochemical |
| 6. 8-epi prostaglandin $F_2$ [isoprostane] | spectrophotometric/immunochemical |
| 7. creatinine | spectrophotometric/chemical |
| Prooxidant Potential | |
| 8. Total iron | |
| 9. Available iron binding capacity [AIBC] | spectrophotometric |
| 10. Total iron binding capacity [TIBC] | |
| 11. % iron saturation | |
| 12. Ferritin | homogeneous EIA/chemical |
| 13. Copper | bathocuproine technique or ICP-MS |
| 14. Ceruloplasmin | immunoprecipitation (turbidimetric) |
| Glycation Potential | |
| 15. Glucose | spectrophotometric/chemical |
| 16. Glycated Protein (Fructosamine) | spectrophotometric/chemical |
| Total Antioxidants | |
| 17. Oxygen Radical Absorption Capacity [ORAC] | fluorescent/chemical |
| 18. Aqueous ORAC | fluorescent/chemical |
| 19. Lipid ORAC | fluorescent/chemical |
| 20. Lipid Peroxidation Inhibition Capacity [LPIC] | spectrophotometric/chemical |
| Water-soluble Antioxidants | |
| 21. Vitamin C [Ascorbate] | spectrophotometric/chemical |
| 22. Thiols | spectrophotometric/chemical |
| 23. Uric acid | spectrophotometric/chemical |
| 24. Direct & Total bilirubin | spectrophotometric/chemical |
| Lipid-soluble Antioxidants | |
| 25. Lutein | HPLC |
| 26. Zeaxanthin | HPLC |
| 27. β-Cryptoxanthin | HPLC |
| 28. Lycopene | HPLC |
| 29. β-Carotene | HPLC |
| 30. α-Carotene | HPLC |
| 31. Retinol [Vitamin A] | HPLC |
| 32. Retinyl Palmitate | HPLC |
| 33. Carotenoid classes | HPLC |
| 34. α-Tocopherol [vitamin E] | HPLC |
| 35. δ-Tocopherol [vitamin E] | HPLC |
| 36. γ-Tocopherol [vitamin E] | HPLC |
| 37. Tocopherol/(Cholesterol + TG) ratio | |
| 38. Ubiquinol [Coenzyme Q10] | HPLC |
| Lipids and Proteins | |
| 39. Cholesterol | Abell-Kendall assay/chemical |
| 40. Triglycerides [TG] | spectrophotometric/chemical |
| 41. Albumin | spectrophotometric/chemical |
| 42. Total Protein | spectrophotometric/chemical |
| 43. Albumin/Globulin ratio | |
| Cardiac Disease Risk Factors Panel | |
| 44. Homocysteine | HPLC |
| 45. Folic acid | homogeneous EIA/chemical |
| 46. Cyanocobalamin [vitamin $B_{12}$] | homogenous EIA/chemical |
| 47. Low density lipoprotein [LDL] | calculated by Friedewald equation |
| 48. High density lipoprotein [HDL] | Abell-Kendall assay/chemical |
| 49. Apolipoprotein B | Turbidimetric/chemical |
| 50. Apolipoprotein A1 | Turbidimetric/chemical |
| Age-related Hormone Panel | |
| 51. 5-Dihydrotestosterone | spectrophotometric/immunochemical |
| 52. 6-Hydroxy melatonin sulfate [6-SM] | spectrophotometric/immunochemical |
| 53. Cortisol | spectrophotometric/immunochemical |
| 54. Dehydroepiandrosterone sulfate [DHEA-S] | spectrophotometric/immunochemical |
| 55. Estradiol | spectrophotometric/immunochemical |
| 56. Insulin-like Growth Factor 1 [IGF-1] | spectrophotometric/immunochemical |
| 57. Progesterone | spectrophotometric/immunochemical |

-continued

| Biomarker | Assay used for determination |
|---|---|
| 58. Testosterone | spectrophotometric/immunochemical |
| 59. Thyroid Stimulating Hormone [TSH] | spectrophotometric/immunochemical |
| 60. Thyroxine [T4] | spectrophotometric/immunochemical |
| Mineral and Trace Element Panel | |
| 61. Aluminium | ICP-MS |
| 62. Antimony | ICP-MS |
| 63. Arsenic | ICP-MS |
| 64. Cadmium | ICP-MS |
| 65. Calcium | ICP-MS |
| 66. Chromium | ICP-MS |
| 67. Cobalt | ICP-MS |
| 68. Copper | ICP-MS |
| 69. Iodine | ICP-MS |
| 70. Iron | ICP-MS |
| 71. Lead | ICP-MS |
| 72. Magnesium | ICP-MS |
| 73. Manganese | ICP-MS |
| 74. Mercury | ICP-MS |
| 75. Molybdenum | ICP-MS |
| 76. Nickel | ICP-MS |
| 77. Selenium | ICP-MS |
| 78. Sulfur | ICP-MS |
| 79. Strontium | ICP-MS |
| 80. Tin | ICP-MS |
| 81. Vanadium | ICP-MS |
| 82. Zinc | ICP-MS |

EIA - enzyme immunoassay;
HPLC - high performance liquid chromatography;
ICP-MS - inductive coupled plasma -mass spectrometry.

Figure 3:
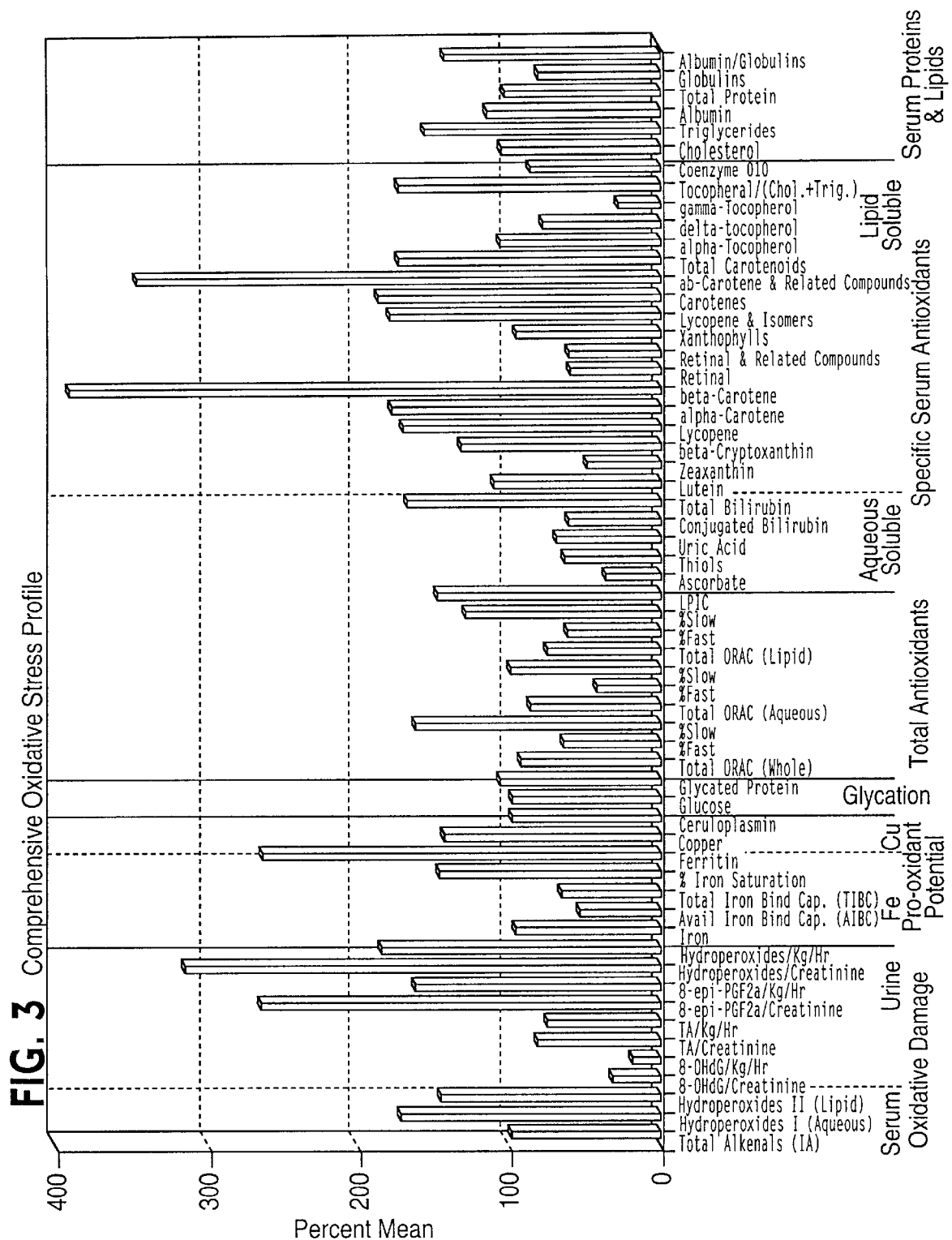
FIG. 3 is a Comprehensive Oxidative Stress Profile.

Comprehensive oxidative stress profile obtained for a patient is shown in FIG. 3 and Table 1.

TABLE 1

Comprehensive Oxidative Stress Profile

| Parameters | Assay CV (%) | Reference range | Units | Mean | Patient Value | Percent of Mean |
|---|---|---|---|---|---|---|
| Oxidative Damage | | | | | | |
| Serum | | | | | | |
| Total alkenals | 5.0 | 0.5–4.1 | μM | 2.0 | 2.0 | 100 |
| Hydroperoxides (aqueous) | 3.7 | 0.3–3.2 | μM | 1.0 | 1.8 | 175 |
| Hydroperoxides (lipid) | 3.1 | 1.6–2.4 | μM | 2.0 | 2.9 | 145 |
| Urine | | | | | | |
| 8-hydroxy deoxyguanosine [8-OH dG] | 4.9 | 0–75 | ng/ml | 38 | 5.9 | 16 |
| 8-OH dG/creatinine | 4.3 | 0–1.3 | *** | 0.37 | 0.05 | 13 |
| 8-OH dG/kg (lean BW)/hr | 4.3 | 0–100 | ng/kg/hr | 61.4 | 12.4 | 20 |
| Total alkenals | 6.5 | 3.5–25.0 | μM | 11.0 | 7.6 | 69 |
| Total alkenals/creatinine | 5.1 | 0.06–0.43 | *** | 0.11 | 0.061 | 56 |
| Total alkenals (lean BW)hr | 6.2 | 4.7–33.5 | μM/kg/hr | 18.1 | 13.8 | 76 |
| 8-epi PGF$_{2\alpha}$ | 3.1 | 0–3500 | pg/ml | 1750 | 1085 | 62 |
| 8-epi PGF$_{2\alpha}$/creatinine | 2.8 | 0–60.7 | *** | 17.2 | 8.7 | 51 |
| 8-epi PGF$_{2\alpha}$/kg (lean BW)/hr | 6.8 | 0–4667 | pg/kg/hr | 2865 | 2620 | 91 |
| hydroperoxides II (lipid) | 5.0 | 5.1–15.1 | μM | 7.4 | 14.2 | 192 |
| hydroperoxides/creatinine | 4.3 | 0.09–0.26 | *** | 0.07 | 0.11 | 157 |
| hydroperoxides/kg (lean BW)/hr | 5.8 | 6.8–20.1 | μM/kg/hr | 12.1 | 22.5 | 186 |
| creatinine | 3.6 | 58–146 | mg/dl | 102 | 125 | 123 |
| Prooxidant Potential | | | | | | |
| Iron Status | | | | | | |
| Iron | 5.5 | 35–140 | μg/dl | 88 | 92 | 105 |
| Avail. iron binding capacity | 4.4 | 130–375 | μg/dl | 253 | 140 | 55 |
| Total iron binding capacity | 5.0 | 245–400 | μg/dl | 340 | 232 | 68 |
| % iron saturation | 5.0 | 13–45 | % | 26 | 40 | 154 |
| ferritin | 6.2 | 30–480 (men) 2–212 (women) | ng/ml | 63 | 166 | 265 |

TABLE 1-continued

Comprehensive Oxidative Stress Profile

| Parameters | Assay CV (%) | Reference range | Units | Mean | Patient Value | Percent of Mean |
|---|---|---|---|---|---|---|
| Copper Status | | | | | | |
| Copper | 4.6 | 70–140 | µg/dl | 101 | 146 | 145 |
| Ceruloplasmin | 3.7 | 150–630 | mg/dl | 236 | 239 | 101 |
| Glycation | | | | | | |
| Glucose | 0.9 | 78–115 | mg/dl | 90 | 89 | 99 |
| Glycated protein | 2.4 | 174–286 | µM | 236 | 251 | 106 |
| Total Antioxidants | | | | | | |
| Whole ORAC | | | | | | |
| Total ORAC | 3.4 | 3300–5000 | µM | 4386 | 4096 | 93 |
| % Fast | 3.1 | 300–600 | µM | 496 | 325 | 66 |
| % Slow | 2.9 | 1500–2300 | µM | 1746 | 2840 | 163 |
| Aqueous Soluble Fraction | | | | | | |
| Total ORAC | 2.0 | 480–1000 | µM | 752 | 663 | 88 |
| % Fast | 2.1 | 150–510 | µM | 349 | 152 | 44 |
| % Slow | 2.2 | 310–750 | µM | 554 | 560 | 101 |
| Lipid Soluble Fraction | | | | | | |
| Total ORAC | 3.7 | 960–1910 | µM | 1520 | 1162 | 76 |
| % Fast | 3.9 | 25–75 | µM | 60 | 38 | 63 |
| % Slow | 3.7 | 190–900 | µM | 430 | 560 | 130 |
| Lipid Peroxidation | | | | | | |
| Inhibition Capacity (LPIC) | 1.1 | 45–85 | % | 55 | 89 | 162 |
| Specific Serum Antioxidants | | | | | | |
| Water-soluble antioxidants | | | | | | |
| Ascorbate | 2.0 | 7.0–26.5 | µg/ml | 13.0 | 5.0 | 38 |
| Thiols | 2.2 | 105–230 | µM | 200 | 10.6 | 65 |
| Uric acid | 1.8 | 3.5–7.7 (men) 2.5–6.8 (women) | mg/dl | 5.1 | 3.6 | 71 |
| Conjugated bilirubin | 3.3 | 0–0.65 | mg/dl | 0.30 | 0.41 | 63 |
| Total bilirubin | 3.5 | 0.1–1.2 | mg/dl | 0.65 | 1.1 | 169 |
| Specific carotenoids | | | | | | |
| Lutein | 3.3 | 0.05–0.57 | µg/ml | 0.17 | 0.19 | 112 |
| Zeaxanthin | 2.6 | 0.02–0.13 | µg/ml | 0.04 | 0.02 | 50 |
| β-Cryptoxanthin | 2.2 | 0.007–0.18 | µg/ml | 0.06 | 0.08 | 133 |
| Lycopene | 1.8 | 0.01–0.33 | µg/ml | 0.18 | 0.31 | 172 |
| α-Carotene | 4.0 | 0.01–0.37 | µg/ml | 0.05 | 0.09 | 180 |
| β-Carotene | 1.6 | 0.07–0.68 | µg/ml | 0.19 | 0.75 | 395 |
| Retinol | 3.6 | 0.35–1.25 | µg/ml | 0.65 | 0.40 | 62 |
| Retinyl palmitate | 2.3 | 0.01–0.17 | µg/ml | 0.07 | 0.06 | 86 |
| Carotenoid Classes | | | | | | |
| Retinol and related compounds | 11.0 | 0.35–1.25 | µg/ml | 0.67 | 0.42 | 63 |
| Xanthophylls | 2.0 | 0.43–1.00 | µg/ml | 0.69 | 0.67 | 97 |
| Lycopene and isomers | 4.0 | 0.18–0.50 | µg/ml | 0.36 | 0.65 | 181 |
| Carotenes | 8.0 | 0.06–0.13 | µg/ml | 0.09 | 0.17 | 189 |
| α,β-Carotene & related compounds | 2.0 | 0.15–0.52 | µg/ml | 0.26 | 0.91 | 350 |
| Total carotenoids | 3.0 | 1.68–2.74 | µg/ml | 2.07 | 2.21 | 107 |
| Tocopherols | | | | | | |
| α-Tocopherol | 5.6 | 6.5–17.2 | µg/ml | 10.1 | 17.7 | 175 |
| δ-Tocopherol | 33 | 0.06–0.2 | µg/ml | 0.1 | 0.08 | 80 |
| γ-Tocopherol | 8.2 | 0.7–4.6 | µg/ml | 2.0 | 0.6 | 30 |
| Total tocopherol/(Cholesterol + Triglycerides) | 2.7 | 0.013–0.125 | | 0.04 | 0.07 | 175 |
| Coenzyme Q10 | 6.9 | 0.6–1.0 | µg/ml | 0.8 | 0.7 | 88 |
| Serum Proteins & Lipids | | | | | | |
| Albumin | 1.3 | 2.2–5.0 | g/dl | 4.5 | 5.2 | 116 |
| Total protein | 2.1 | 6.0–8.2 | g/dl | 7.3 | 7.5 | 103 |
| Globulins | 1.7 | 1.0–6.0 | g/dl | 2.8 | 2.3 | 82 |
| Albumin/Globulins | 1.7 | 0.37–5.0 | g/dl | 1.6 | 2.3 | 144 |
| Cholesterol | 1.5 | 130–280 | mg/dl | 200 | 210 | 105 |
| Triglycerides | 1.0 | 30–190 | mg/dl | 100 | 157 | 157 |

Figure 4:
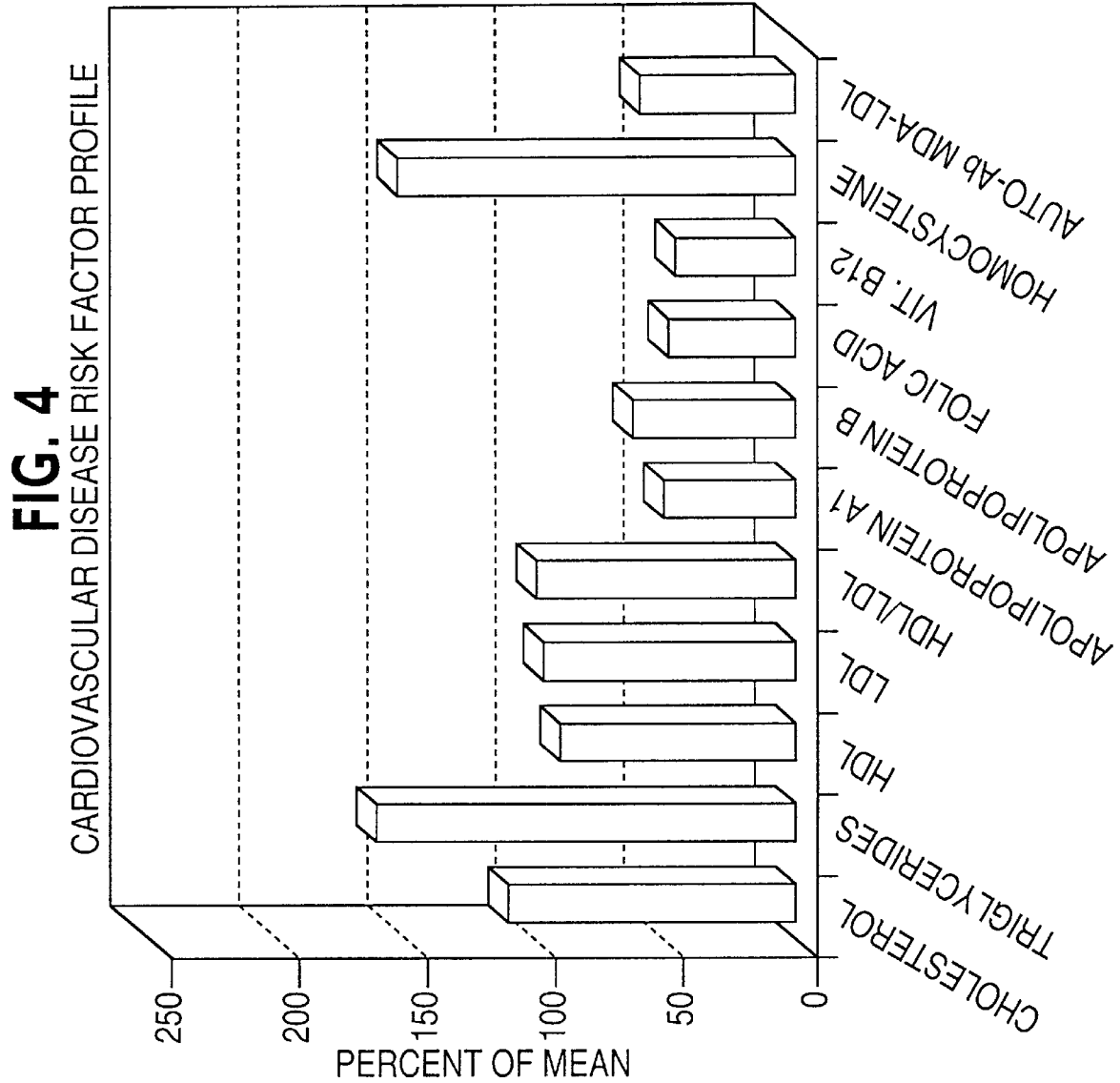
FIG. 4 is a Cardiovascular Disease Risk Factor Profile.

Typical cardiovascular risk factor profile is shown in FIG. 4 and Table 2.

TABLE 2

Cardiovascular Risk Factor Profile

| Parameter | Assay CV (%) | Reference range | Units | Mean | Patient Value | Percent of Mean* |
|---|---|---|---|---|---|---|
| Cholesterol | 1.5 | 130–280 | mg/dl | 200 | 218 | 109 |
| Triglycerides | 1.0 | 30–190 | mg/dl | 100 | 162 | 162 |
| High density lipoproteins [HDL] | 1.5 | 29–80 | mg/dl | 63 | 58 | 92 |
| Low density lipoproteins [LDL] | 2.4 | 95–160 | mg/dl | 130 | 128 | 98 |
| HDL/LDL | 2.1 | 0.15–0.85 | *** | 0.45 | 0.5 | 101 |
| Apolipoprotein A1 | 2.6 | 73–169 | mg/dl | 134 | 68 | 51 |
| Apolipoprotein B | 2.6 | 58–138 | mg/dl | 88 | 55 | 63 |
| Folic acid | 2.4 | 3.3–17.8 | ng/ml | 12.5 | 6.2 | 50 |
| Vitamin $B_{12}$ | 1.9 | 236–1000 | pg/ml | 825 | 387 | 47 |
| Homocysteine | 2.6 | 7.2–22.1 | uM/L | 12.2 | 18.7 | 153 |
| Autoantibody to MDA-LDL | 4.0 | 37–1200 | mU/ml | 544.0 | 314 | 58 |

*Values have been corrected for age and sex-levels based on healthy age-heterogenous population.

Age-related hormone profile is shown in FIG. 5 and Table 3.

TABLE 3

Age-related Hormone Profile

| Parameter | Assay CV (%) | Reference range | Units | Mean | Patient value | Percent of Mean* | Percent of Peak |
|---|---|---|---|---|---|---|---|
| DHEA-S | 5.2 | 0.3–3.35 | ug/ml | 1.1 | 2.8 | 258 | 63 |
| Estradiol (total) | 5.7 | 2.2–49.5 | pg/ml | 30 | 52 | 173 | 15 |
| Testosterone (total) | 3.1 | 1.2–12.0 | ng/ml | 5.3 | 6.0 | 113 | 69 |
| 5α dihydrotestosterone (5α DHT) | 5.4 | 250–750 | pg/ml | 520 | 630 | 121 | 58 |
| Progesterone | 5.2 | 0.1–28.1 | ng/ml | 9.8 | 3.6 | 37 | 18 |
| Insulin Growth Factor-1 [Growth Horomone] | 3.2 | 8.0–580.0 | ng/ml | 225 | 321 | 142 | 52 |
| 6-sulfatoxy melatonin [Melatonin; urine] | 4.3 | 7.9–16.2 | ng/ml | 11 | 12.3 | 112 | 54 |
| Melatonin/creatinine | 3.9 | 0.14–0.28 | *** | 0.19 | 0.10 | 53 | 46 |
| Melatonin/kg (lean BW)/hr | 3.1 | 10.5–21.6 | ng/kg/hr | 14.7 | 11 | 72 | 37 |
| Cortisol | 2.4 | 5.2–30.5 | μg/dl | 12.7 | 15.1 | 119 | 87 |
| T3 | 3.0 | 230–420 | pg/dl | 360 | 290 | 81 | 54 |
| T4 | 3.4 | 4.5–12.0 | μg/dl | 6.5 | 7.3 | 112 | 64 |
| TSH | 4.1 | 0.40–4.82 | mU/ml | 2.1 | 1.3 | 60 | 48 |

*Values have been corrected for age and sex levels base on healthy age-heterogenous population.

Figure 6B:
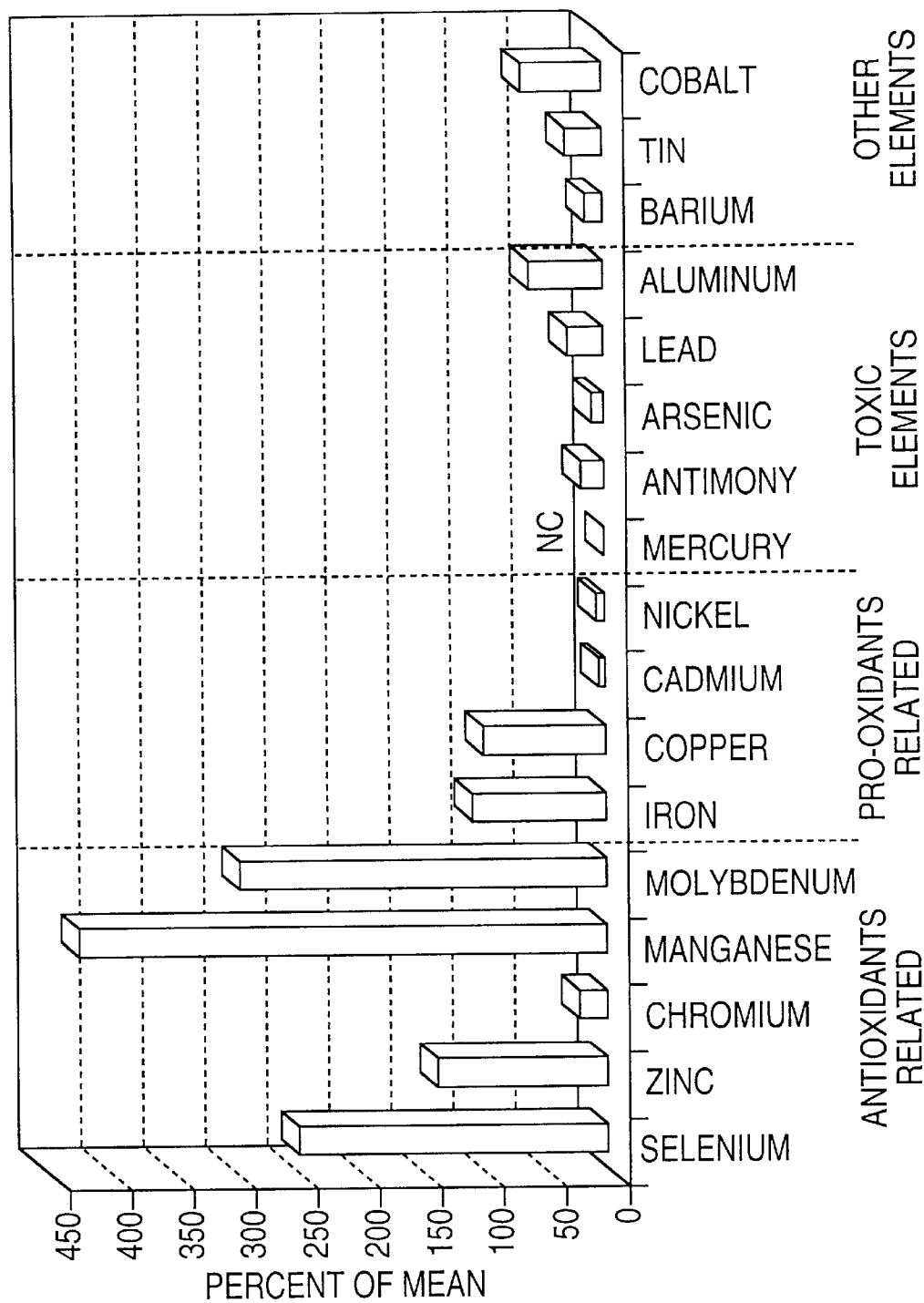
FIG. 6(b) is a Trace Element Profile with respect to Serum.
Figure 7A:
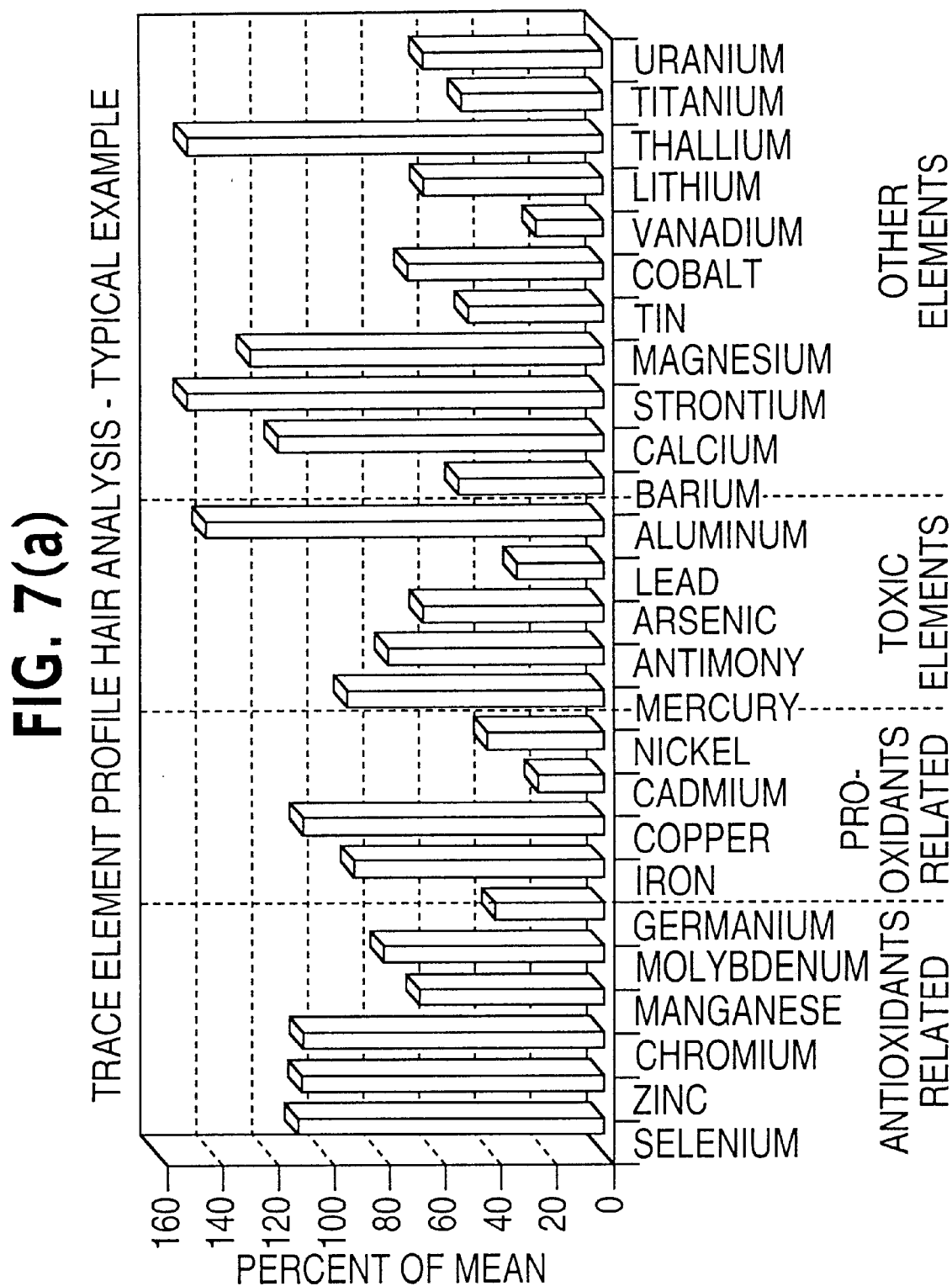
FIG. 7(a) is a Trace Element Profile with respect to Hair.

Trace element profile for typical sample of urine and serum is shown in FIG. 6a and 6b respectively. Trace element profile for typical sample of hair and drinking water is shown in FIG. 7a and 7b respectively.

Figure 2:
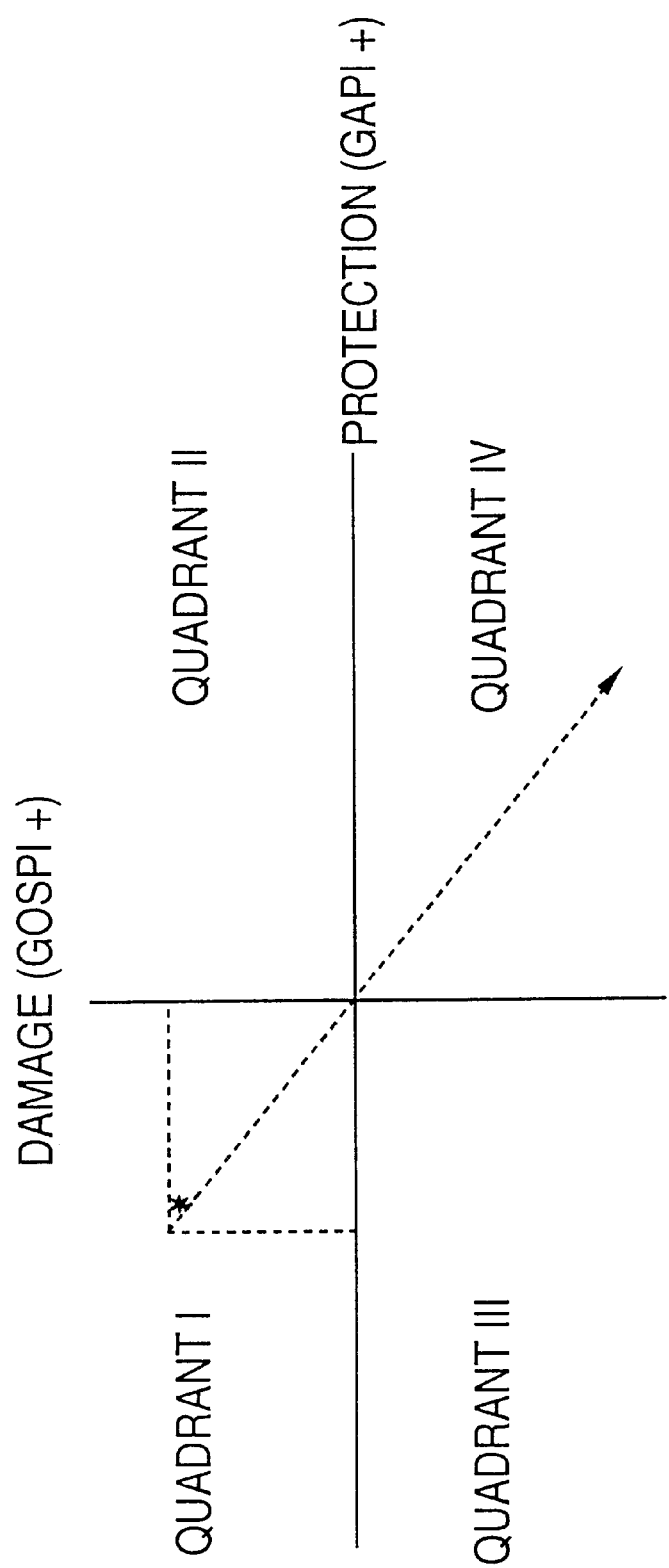
FIG. 2 is a protocol showing the Oxidative Stress Profile Diagnostic Plot.
Figure 8:
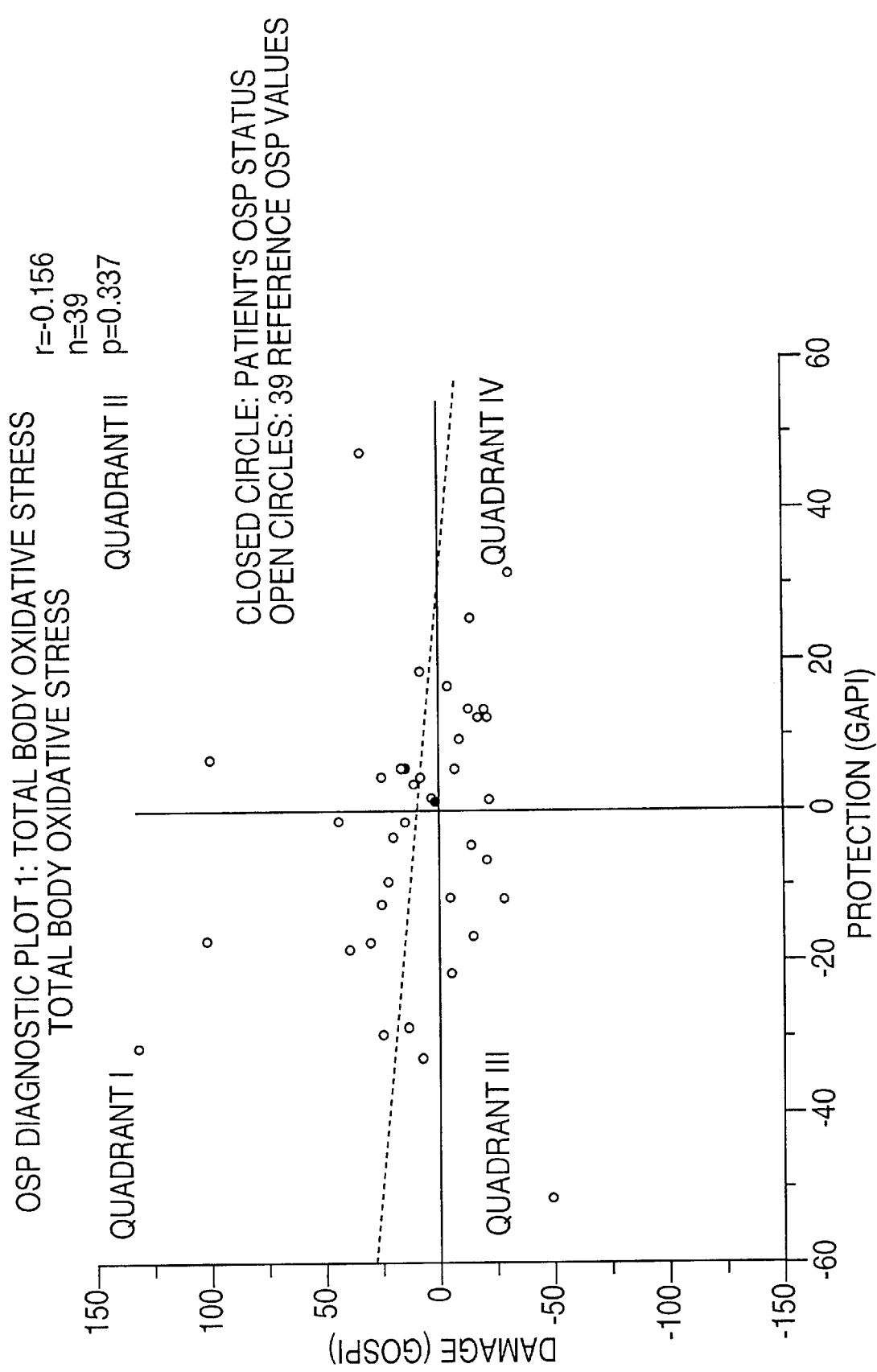
FIG. 8 is an Oxidative Stress Profile (OSP) Diagnostic Plot 1: Total Body Oxidative Stress.
Figure 9:
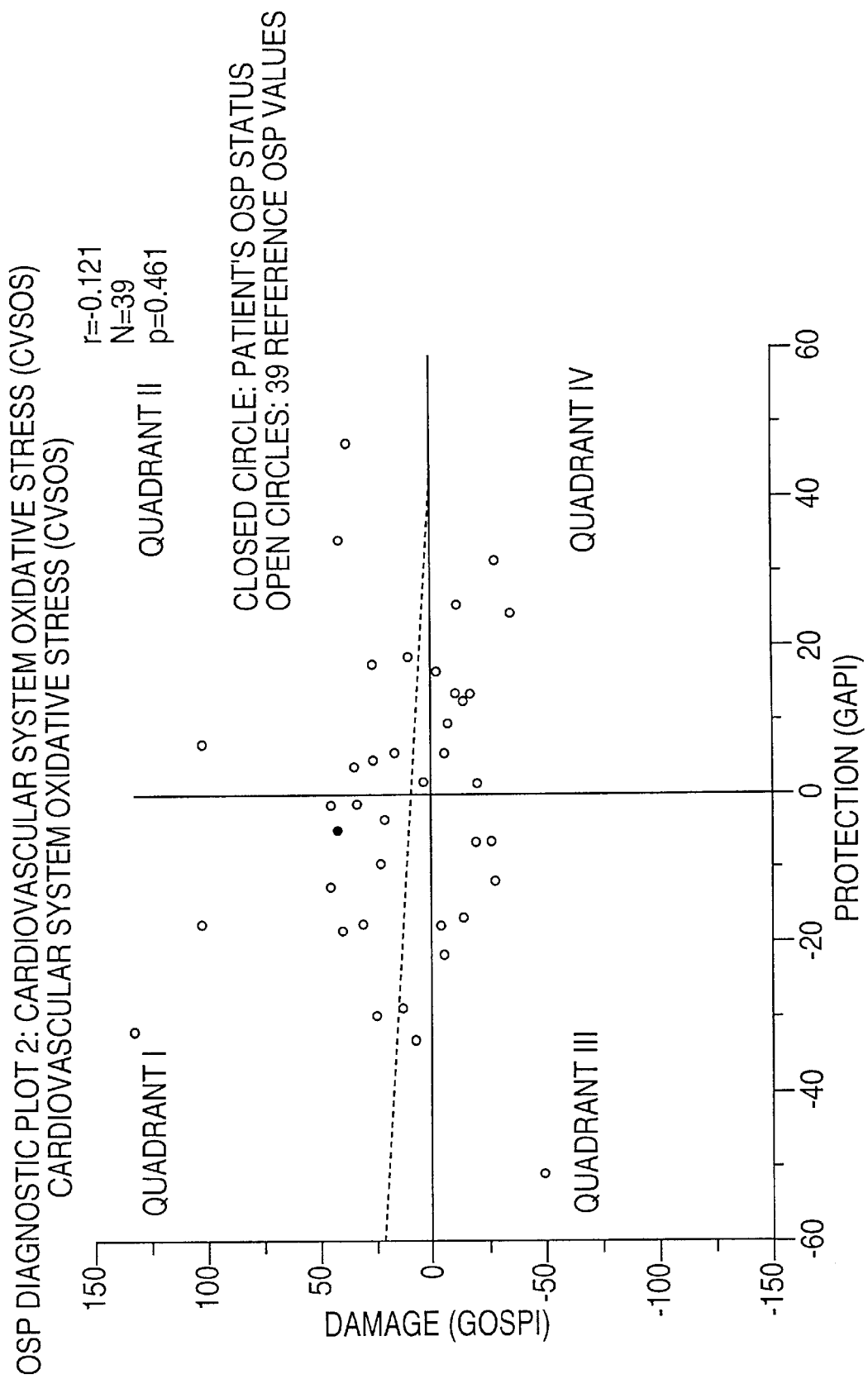
FIG. 9 is an Oxidative Stress Profile (OSP) Diagnostic Plot 2: Cardiovascular System Oxidative Stress (CVSOS)

From these primary data, the oxidative stress profile diagnostic plot can be drawn, as shown in FIG. 2, with Genox oxidative stress profile index (GOSPI) in ordinate and Genox antioxidant profile index (GAPI) in abscissa. The patient's specific OSP status may be positioned in one of the four quadrants of this diagnostic plot. FIGS. 8, 9 and 10 show typical examples of a patient's OSP status, in which the patient's OSP status is compared with 39 reference OSP values.

A new technique to measure the oxidative stress status (OSS) of humans using small samples of urine, serum and saliva This new technique is based on the integration of different but complimentary biochemical assays. The result is an unusually high degree of reliability in the measurement of oxidative stress and antioxidant status of an individual. A physician in determining what intervention procedures are indicated for his patient can then use this information with greater confidence.

The application of the profiling concept to obtain an unusually high reliable data of the oxidative stress status of an individual and also detailed information suggesting possible intervention therapies. In this procedure 82 different biochemical assays are used, which are selected on the basis of their accuracy, reliability and cost (ability to apply mass production economies) to measure both oxidative stress and antioxidant status of an individual. The choice of a specific array of these assays allows the application of their integration and a reductive analysis procedure to obtain a reliable and representative final result.

A diagnostic plot to assist the physician in the reading and interpretation of the comprehensive oxidative stress profile, to understand the relationship between the patient's oxidative stress status and their antioxidant status. How an individual'sbody is coping with the factors controlling an individual's OSS is very complex. It is clear that an individual's heredity, lifestyle and environmental factors are the key controlling elements. Genetics largely controls the level of endogenous generation of reactive oxygen species as well as the level of protective and repair processes in tissues. An individual's compensatory mechanism governing tissue levels of antioxidants to maintain their normal homeostasis oxidative stress state is a yet to be recognized complicating factor in the relationship between the patients oxidative stress status and their antioxidant status. It is our finding that in many individuals the level of antioxidant status is positively, and not negatively, correlated with the amount of oxidative damage they have or their oxidative stress state. This finding implies that high tissue levels of antioxidants may be indicative of high endogenous levels of tissue oxidative damage and not lower levels, as has been frequently assumed by some diagnostic laboratories in the past. To extract information from multitude of assays, interpret its meaning and then to provide the patients with how they might best take action to lower their oxidative stress state, a new technique called the diagnostic plot has been developed.

This is what is described as the Genox Oxidative Stress Profile Diagnostic Plot (GOSP Diagnostic Plot). It is based on the calculations of two key parameters from an individual's OSS. The two key parameters introduced are, Genox Oxidative Stress Profile Index (GOSPI) and Genox Antioxidant Profile Index (GAPI). These two parameters are calculated as follows:

$$GOSPI = 1/n \, \Box (\text{Percent of Mean} - 100\%)$$

$$GAPI = 1/n \, \Box (\text{Percent of Mean} - 100\%)$$

In both GOSPI and GAPI, n is equal to the number of assays in the sum. GOSPI is calculated from 8–10 of the oxidative damage and prooxidant potential assays. GAPI is calculated from 20–30 of the antioxidant assays. The resulting plot, as shown in FIG. 2 with GOSPI in ordinate and GAPI in abscissa, is described as the Genox Oxidative Stress Profile Diagnostic Plot.

A diagnostic plot to assist the physician in the specific analysis of the oxidative stress of the patients suffering from cardiovascular system disorders. In this plot, only those factors of oxidative stress and antioxidants that deal with cardiovascular system is taken into consideration. The result provides the physician with an accurate risk analysis known for cardiovascular disease, in addition to suggested intervention therapies.

An estimation of the general health status of the individual, based on the integration of overall data of indicators for cardiovascular system, age-dependent hormone and trace metal panels.

A diagnostic plot derived from the measurement of 82 assays which characterize two key parameters which significantly contribute to an individual's health status. These two parameters are oxidative stress profile (OSP) and antioxidant profile. Each of the assays which constitute the 82 assays are complimentary with other assays of the profile, thus providing either confirmation information or the synthesis of new information. The diagnostic plot, developed to interpret the assay data which provides information about oxidative damage and antioxidant protection, consists of four quadrants, each with noticeable characteristics. By visually assessing the position of a patient's OSP status, in comparison to reference OSP values in the four quadrants constituting the diagnostic plot, physicians and other health care professionals can provide sound advice to their patients regarding dietary and life style changes one need to adhere for prevention of oxidative stress-related diseases as well as postponing premature aging processes.

What is claimed is:

1. A method of assessing the oxidative stress state of an individual comprising performing on said individual between 8 and 10 first assays for oxidative stress and prooxidant potential, said assays selected from a first group of assays for:
   (a) total alkenals
   (b) aqueous hydroperoxides
   (c) lipid hydroperoxides
   (d) auto-antibody oxidized low density lipoproteins
   (e) 8-hydroxy deoxyguanosine
   (f) 8-epi-prostaglandin F2
   (g) creatinine
   (h) total iron
   (i) available iron binding capacity
   (j) total iron binding capacity
   (k) percent iron saturation
   (l) ferritin
   (m) copper
   (n) ceruloplasmin; calculating a first parameter Genox Oxidative Stress Profile Index (GOSPI), from 8 to 10 assays according to the formula:
   GOSPI—$1/n \, \Theta(\text{Percent of Mean} - 100\%)$, where n is equal to the number of assays in the sum; and performing on said individual at least 20 assays for antioxidants, said antioxidant selected from a second group of assays for:

calculating a second parameter, the Genox Antioxidant Profile Index (GAPI), from at least 20 antioxidant assays selected from a second group consisting of:
   (i) oxygen radical absorption capacity (ORAC)
   (ii) aqueous ORAC
   (iii) lipid ORAC
   (iv) lipid peroxidation inhibition capacity (LPIC)
   (v) vitamin C
   (vi) thiols
   (vii) uric acid
   (viii) direct and total bilirubin
   (ix) lutein
   (x) zeaxanthin
   (xi) β-cryptoxanthin
   (xii) lycopene
   (xiii) α-carotene
   (xiv) β-carotene
   (xv) retinol
   (xvi) retinyl palmitate
   (xvii) carotenoid classes
   (xviii) α-tocopherol
   (xix) δ-tocopherol
   (xx) γ-tocopherol
   (xxi) tocopherol/(cholesterol+triglycerides)
   (xxii) ubiquinol calculating a second parameter the Genox Antioxidant Profile Index (GAPI), from at least 20 antioxidant assays from results of said at least 20 antioxidant assays according to the formula:

GAPI=$1/n \, \Sigma(\text{Percent of Mean} - 100\%)$, where n is equal to the number of assays in the sum;

plotting calculated GOSPI and GAPI in a graph provided by X axis expressing GAPI and Y axis expressing GOSPI; and determining where the individual's calculated GOSPI and GAPI is plotted in the four quadrants divided by XY axes as follows:

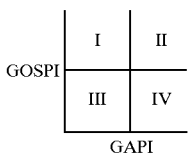

wherein in:

Quadrant I, individuals have the expected high level of oxidative stress that accompanies low levels of antioxidants and therefore, they are expected to respond to higher dosages of antioxidants, to lower their oxidative stress state;

Quadrant II, individuals have high oxidative stress levels in spite of above average levels of antioxidant protection and this condition could develop as a result of stress occurring due to, (a) high levels of iron and/or copper stress
(b) high levels of inflammatory related disease such as caused by an microorganism infections
(c) pharmacological drugs that block antioxidant absorption or synthesis or generate reactive oxygen species
(d) alcoholism
(e) exposure to toxic environmental factors
(f) oxidative stress related diseases;

Quadrant III, individuals have lower than normal oxidative stress state, but with a low antioxidant state which suggests that future improvements can be realized through increasing the antioxidant levels; and Quadrant IV, individuals have lower than normal oxidative stress state, with the expected accompaniment of higher than normal levels of antioxidant protection and further improvement may be indicated by increasing antioxidants in diet, or possibly lowering endogenous production of antioxidants.

* * * * *